United States Patent [19]
Golubev et al.

[11] Patent Number: 5,534,258
[45] Date of Patent: Jul. 9, 1996

[54] POLYPEPTIDES TO PREVENT ATHEROSCLEROTIC PLAQUE

[75] Inventors: Daniel B. Golubev, Jackson Heights, N.Y.; Alexander Chaihorsky, Garfield, N.J.

[73] Assignee: Bio-Virus Research Incorporated, San Mateo, Calif.

[21] Appl. No.: 281,702

[22] Filed: Jul. 27, 1994

[51] Int. Cl.$^6$ .......................... A61K 39/245; A61K 38/00; A61K 39/25; A61K 39/295
[52] U.S. Cl. ..................................... 424/231.1; 424/230.1; 424/202.1; 424/229.1; 514/12
[58] Field of Search ............................. 424/231.1, 230.1, 424/202.1, 229.1; 514/12, 824; 350/300, 324

[56] References Cited

U.S. PATENT DOCUMENTS 4,038,381 7/1977 Perlant ........................................ 424/89

OTHER PUBLICATIONS

Melnick et al. 1990. Possible Role of Cyromegalovirus in Atherogenesis. JAMA. 263(16): 2204–2207.
Petrie et al. 1987. Nucleic Acid Sequences of Cytomegalovirus in Cells . . . J. Infect. Dis. 155(1): 158–159.
Weston et al. 1986. Sequence of the Short Unique Region, Short Repeats . . . J. Gol. Biol. 192: 177–208.
Fabricant et al. 1983. Herpesvirus–Induced Atherosclerosis in Chickens. FASEB, Fed. Proc. 42: 2476–79.
Fabricant et al. 1981. Vaccination Prevents Atherosclerosis Induced by Marek's . . . FASEB Mtg. Abstract p. 335, Abs #583.
McGloch et al. 1986. Complete DNA Sequence of the Short Repeat Region in the Genone . . . Nucleic Acids Res. 14(4): 1727–45.
Lerner et al. In: Biology of Immunologic Disease ed. Dixon et al. pp. 331–338.
Hendrix et al. 1989. The Presence of Cyoomegalovirus Nucleic Acids in Arterial Walls . . . Am. J. Pathol. 134(5): 1151–57.
Benditt et al. 1983. Viruses in the Etiology of Atherosclerosis PNAS, USA. 80: 6386–89.
Fabricant et al. 1978. Virus–Induced Atherosclerosis J. Exp. Med. 148: 335–40.
Hendrix et al. 1990. High Prevalence of Latently Present Cytomegalovirus . . . ATN. J. Pathol. 136: 23–28.

Primary Examiner—James C. Housel
Assistant Examiner—N. M. Minnifield
Attorney, Agent, or Firm—Herbert Dubno; Jonathan Myers

[57] ABSTRACT

A vaccine is disclosed for the prophylaxis against pathogenic development of atherosclerotic plaque in a mammalian subject susceptible thereto which comprises:

(a) 10 to 30% by weight of the compound

Ala Pro Leu Pro Ala Pro Ala Pro Pro Ser Thr Pro Pro Gly     (Seq ID 2)
 1            5              10

Pro Glu Pro Ala Pro Ala Gln Pro Ala Ala Pro Arg Ala Ala ;
    15           20           25

(b) 10 to 30% by weight of the compound

Ala Pro Pro Glu Ala Asp Ala Arg Thr Leu Arg Arg          (Seq ID 4)
 1            5             10

Pro Gly Pro Pro Leu Pro Leu Pro Pro Ser Leu Leu Pro;
     15          20           25

(c) 10 to 30% by weight of the compound

Gly Thr Asp Gly Pro Ala Arg Gly Gly Gly Ser Gly          (Seq ID 6)
 1            5              10

Gly Gly Arg Gly Pro Gly Gly Gly Arg Gly Gly Pro Arg Gly;
    15            20           25 and (d) 10 to 30% by weight of the compound

Gly Trp Ala Ala Arg Arg Gly Arg Arg Arg Gly Arg          (Seq ID 8)
 1            5              10

Arg Arg Gly Arg Arg Arg Arg Gln Arg Arg Ala Ala Arg Arg
    15           20            25

Arg Arg;

in combination with a pharmaceutically acceptable inert carrier.

2 Claims, 1 Drawing Sheet

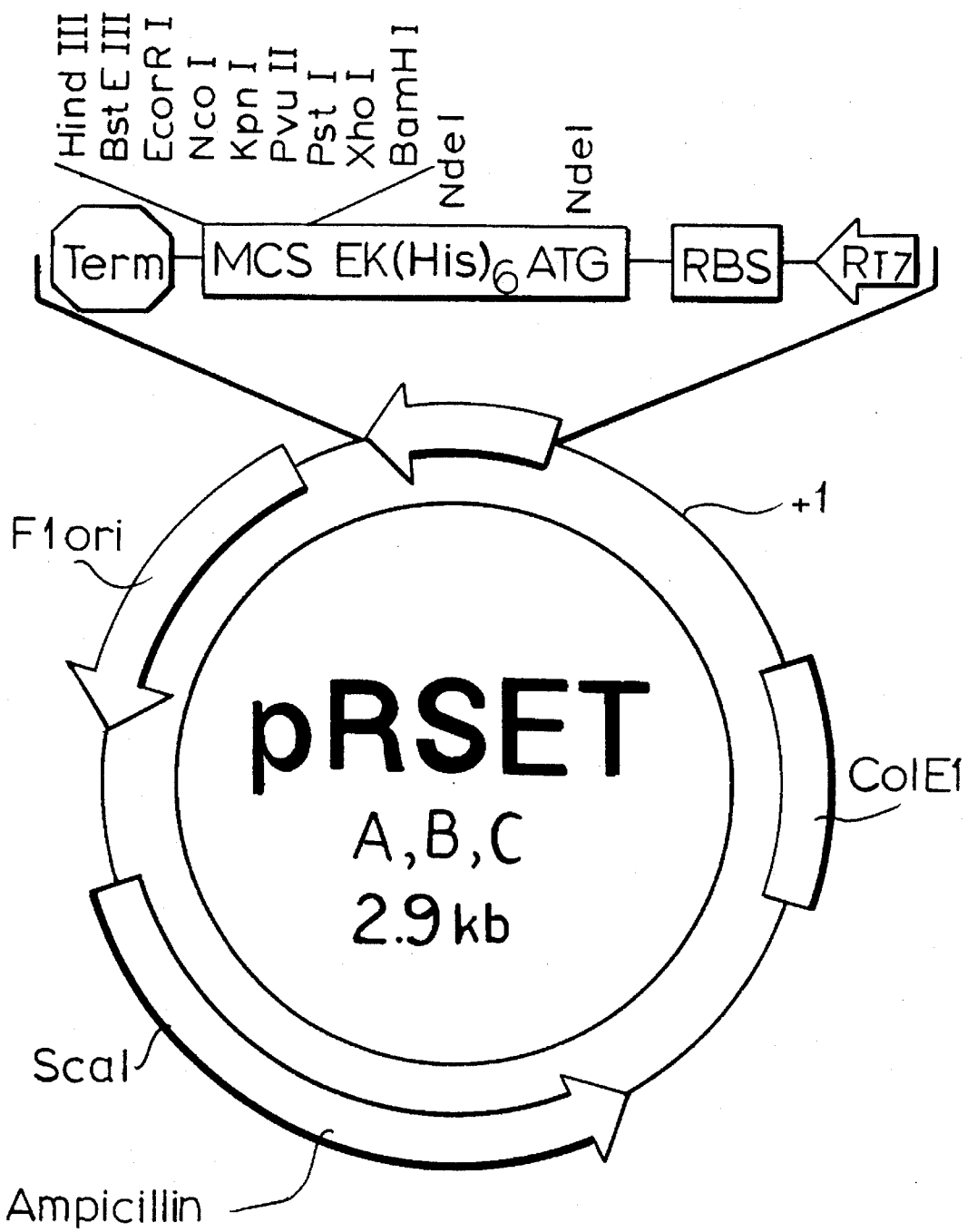
G. pRSET Vector Map
PRIOR ART

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
            ( A ) LENGTH: 84 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
            ( A ) NAME/KEY: CDS
            ( B ) LOCATION: 1..84

( x i ) SEQUENCE DESCRIPTION: SEQ ID NO:1:

```
GCC  CCC  CTC  CCC  GCG  CCC  GCG  CCC  CCC  TCC  ACG  CCC  CCG  GGG  CCC  GAG      48
Ala  Pro  Leu  Pro  Ala  Pro  Ala  Pro  Pro  Ser  Thr  Pro  Pro  Gly  Pro  Glu
 1                   5                             10                   15

CCC  GCC  CCC  GCC  CAG  CCC  GCG  GCG  CCC  CGG  GCC  GCC                          84
Pro  Ala  Pro  Ala  Gln  Pro  Ala  Ala  Pro  Arg  Ala  Ala
          20                             25
```

( 2 ) INFORMATION FOR SEQ ID NO:2:

( i ) SEQUENCE CHARACTERISTICS:
            ( A ) LENGTH: 28 amino acids
            ( B ) TYPE: amino acid
            ( D ) TOPOLOGY: linear ( i i ) MOLECULE TYPE: peptide ( x i ) SEQUENCE DESCRIPTION: SEQ ID NO:2:

```
Ala  Pro  Leu  Pro  Ala  Pro  Ala  Pro  Pro  Ser  Thr  Pro  Pro  Gly  Pro  Glu
 1                   5                             10                   15

Pro  Ala  Pro  Ala  Gln  Pro  Ala  Ala  Pro  Arg  Ala  Ala
          20                             25
```

( 2 ) INFORMATION FOR SEQ ID NO:3:

( i ) SEQUENCE CHARACTERISTICS:
            ( A ) LENGTH: 75 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
            ( A ) NAME/KEY: CDS
            ( B ) LOCATION: 1..75

( x i ) SEQUENCE DESCRIPTION: SEQ ID NO:3:

```
GCT  CCT  CCA  GAG  GCC  GAC  GCG  CGG  ACC  CTC  CGA  CGT  CCT  GGC  CCG  CCG      48
```

```
Ala  Pro  Pro  Glu  Ala  Asp  Ala  Arg  Thr  Leu  Arg  Arg  Pro  Gly  Pro  Pro
 1              5                        10                        15

CTG  CCG  CTG  CCG  CCT  TCC  CTT  CTC  CCG                                        75
Leu  Pro  Leu  Pro  Pro  Ser  Leu  Leu  Pro
           20                        25
```

( 2 ) INFORMATION FOR SEQ ID NO:4:

( i ) SEQUENCE CHARACTERISTICS:
        ( A ) LENGTH: 25 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Ala  Pro  Pro  Glu  Ala  Asp  Ala  Arg  Thr  Leu  Arg  Arg  Pro  Gly  Pro  Pro
 1              5                        10                        15

Leu  Pro  Leu  Pro  Pro  Ser  Leu  Leu  Pro
           20                        25
```

( 2 ) INFORMATION FOR SEQ ID NO:5:

( i ) SEQUENCE CHARACTERISTICS:
        ( A ) LENGTH: 78 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( i x ) FEATURE:
        ( A ) NAME/KEY: CDS
        ( B ) LOCATION: 1..78

( x i ) SEQUENCE DESCRIPTION: SEQ ID NO:5:

```
GGC  ACC  GAC  GGC  CCC  GCC  CGA  GGA  GGC  GGA  AGC  GGA  GGA  GGA  CGC  GGC    48
Gly  Thr  Asp  Gly  Pro  Ala  Arg  Gly  Gly  Gly  Ser  Gly  Gly  Gly  Arg  Gly
 1              5                        10                        15

CCC  GGT  GGC  GGA  AGA  GGT  GGC  CCC  CGC  GGG                                   78
Pro  Gly  Gly  Gly  Arg  Gly  Gly  Pro  Arg  Gly
           20                        25
```

( 2 ) INFORMATION FOR SEQ ID NO:6:

( i ) SEQUENCE CHARACTERISTICS:
        ( A ) LENGTH: 26 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Gly  Thr  Asp  Gly  Pro  Ala  Arg  Gly  Gly  Gly  Ser  Gly  Gly  Gly  Arg  Gly
 1              5                        10                        15

Pro  Gly  Gly  Gly  Arg  Gly  Gly  Pro  Arg  Gly
           20                        25
```

( 2 ) INFORMATION FOR SEQ ID NO:7:

( i ) SEQUENCE CHARACTERISTICS:
        ( A ) LENGTH: 84 base pairs
        ( B ) TYPE: nucleic acid
        ( C ) STRANDEDNESS: single
        ( D ) TOPOLOGY: linear

```
    ( i i ) MOLECULE TYPE: DNA (genomic)

( i i i ) HYPOTHETICAL: NO ( i v ) ANTI-SENSE: NO ( i x ) FEATURE:
            ( A ) NAME/KEY: CDS
            ( B ) LOCATION: 1..84

( x i ) SEQUENCE DESCRIPTION: SEQ ID NO:7:

GGC  TGG  GCT  GCG  CGG  CGG  GGC  CGG  CGA  CGG  GGA  CGG  CGG  CGG  GGA  CGA        4 8
Gly  Trp  Ala  Ala  Arg  Arg  Gly  Arg  Arg  Arg  Gly  Arg  Arg  Arg  Gly  Arg
 1              5                         .1 0                     1 5

CGT  CGC  CGC  CAG  CGG  CGA  GCG  GCA  CGG  AGA  CGG  AGG                             8 4
Arg  Arg  Arg  Gln  Arg  Arg  Ala  Ala  Arg  Arg  Arg  Arg
               2 0                    2 5

( 2 ) INFORMATION FOR SEQ ID NO:8:

( i ) SEQUENCE CHARACTERISTICS:
            ( A ) LENGTH: 28 amino acids
            ( B ) TYPE: amino acid
            ( D ) TOPOLOGY: linear ( i i ) MOLECULE TYPE: peptide ( x i ) SEQUENCE DESCRIPTION: SEQ ID NO:8:

Gly  Trp  Ala  Ala  Arg  Arg  Gly  Arg  Arg  Arg  Gly  Arg  Arg  Arg  Gly  Arg
 1              5                         1 0                     1 5

Arg  Arg  Arg  Gln  Arg  Arg  Ala  Ala  Arg  Arg  Arg  Arg
               2 0                    2 5
```

POLYPEPTIDES TO PREVENT ATHEROSCLEROTIC PLAQUE

FIELD OF THE INVENTION

This invention relates to a vaccine against herpes virus for the prevention of atherosclerosis. More particularly the invention relates to a herpes vaccine containing homologous peptide sequences to those of the viral DNA found in strains of the herpes virus that affect humans and that acts as a prophylaxis against pathogenic development of atherosclerotic plaque in a mammalian subjected susceptible thereto.

BACKGROUND OF THE INVENTION

It is generally accepted that atherogenesis is triggered by primary injury to the endothelial lining of the arterial walls. This injury is believed to be the result of exposure of the underlying smooth muscle cells to several factors of noninfectious origin (hormones, low density lipoproteins, growth factors, among others). The prevailing view is that human atherosclerosis (AS) is a pleiotropic process with various causes. See Ross, R., The Pathogenesis of Atherosclerosis: An Update, New England J. Med.,314, 488 to 500 (1986).

A fundamentally new etiological factor: herpes virus infection was reported by Fabricant et al, who demonstrated that chickens infected with Marek Disease Virus (MDV) have an unusually high incidence of atherosclerotic plaque (ASP) in the arteries. See Fabricant, C. G. et al, Virus-Induced Cholesterol Crystals, *Science*, 181, 566 to 567 (1973); and Fabricant, C. G. et al, Virus-Induced Atherosclerosis, *J. Exp. Med.*, 148, 335 to 340 (1978). Since that time data have been accumulated suggesting herpes virus in AS in humans. It was shown that different herpes viruses can alter smooth muscle cells lipid metabolism and induce cholesterol and cholesterol ester accumulation in these cells. See Fabricant, C. G. et al, Herpes Virus Infection Enhances Cholesterol and Cholesterol Ester Accumulation in Cultured Arterial Smooth Muscle Cells, *Am. J. Pathol*, 105, 176 to 184 (1981); Fabricant, C. G. et al, Herpes Virus-Induced Atherosclerosis in Chickens, *Fed. Proc.*, 42, 2476 to 2479 (1983); Melnick, J. L. et al, Cytomegalovirus Antigen within Human Arterial Smooth Muscle Cells, *Lancet, ii*, 644 to 647 (1983); Gyorkey, F. et al, Herpesviridae in the Endothelial and Smooth Muscle Cells of Proximal Aorta in Atherosclerotic Patients, *Exp. Mol. Pathol*, 40, 328 to 339 (1984); Hajjar et al, Virus-Induced Atherosclerosis: Herpes Virus Infection Alters Aortic Cholesterol Metabolism and Accumulation, *Am. J. Pathol.*, 122, 62 to 70 (1986); Adam et al, High Levels of Cytomegalovirus Antibody in Patients Requiring Vascular Surgery for Atherosclerosis, *Lancet*, 2, 291 to 293 (1987); Petrie, Association of Herpesvirus/ Cytomegalovirus Infections with Human Atherosclerosis, *Prog. Med. Virol.*, 35, 21 to 42 (1988); Grattan, M. T. et al, Cytomegalovirus Infection is Associated with Cardiac Allograft Rejection and Atherosclerosis, *J. A. Med. Assoc.* 261, 3561 to 3566 (1989); Mc Donald, K. et al, Association of Coronary Artery Disease in Cardiac Transplant Recipients with Cytomegalovirus Infection, *Am. J. Cardiol.*, 64, 359 to 362 (1989); Visser et al, Granulocyte-Mediated Injury in Herpes Simplex Virus-Infected Human Endothelium, *Lab. Invest.*, 60, 296 to 304 (1989); Melnick, J. L. et al, Possible Role of Cytomegalovirus in Atherogenesis, *J. Am. Assoc.*, 263, 2204 to 2207 (1990); Bruggeman, C. A. et al, The Possible Role of Cytomegalovirus in Atherogenesis, *Prog. Med. Virol.*, 38, 1 to 26 (1991); Melnick, J. L. et al, Accelerated Graft Atherosclerosis Following Cardiac Transplantation; Do Viruses Play a Role?, *Clin Cardiol.*, 14 (Supp. II), 21 to 26 (1991); and Hajjar, D. P., Viral Pathogenesis of Atherosclerosis, *Am. J. Pathol.*, 133, 1195 to 1211 (1991).

In addition the DNA of various herpesviruses showed positive hybridization with ASP DNA; see Benditt, E. P. et al, Viruses in the Etiology of Atherosclerosis, *Proc. Natl. Acad. Sci.*, 80, 6386 to 6389 (1983); Pyrzak, R. et al, Detection of Specific DNA Segments of Marek's Disease Herpes Virus in Japanese Quail Susceptible to Atherosclerosis, *Atherosclerosis*, 68, 77 to 85 (1987); Petrie, B. L. et al, Nucleic Acid Sequences of Cytomegalovirus in Cultured Human Arterial Tissue, *J. Inf. Dis.*, 155, 158 to 159 (1987); Yamashiroya, H. M. et al, Herpesviridae in Coronary Arteries and Aorta of Young Trauma Victims, *Am. J. Pathol*, 130, 71 to 79 (1988); and Hendrix, M. G. R. et al, The Presence of Cytomegalovirus Nucleic Acids in Arterial Walls of Patients Suffering From Grade III Atherosclerosis, *Am. J. Pathol.*, 134, 1151 to 1157 (1989).

No systematic attempts to demonstrate a viral presence in ASP by direct isolation of infectious HSV from ASP and by detection of viral replication in ASP by Electron Microscopy have been reported. A viral presence in ASP would explain the presence of HSV-like DNA in ASP, and redirect research to determine the molecular mechanisms of viral involvement in etiology of atherosclerosis. In such a case, the possibility of a contamination of ASP in the blood vessels by HSV also has to be excluded.

None of the above references deals with the preparation of a vaccine against any form of the herpes virus. The following reference deals with the preparation of a herpes vaccine against Marek's Disease Herpes-Virus in chickens: Fabricant, J. et al, Vaccination Prevents Atherosclerosis Induced by Marek's disease Herpesvirus, College of Veterinary Medicine and Medicine, Cornell University, Ithaca and New York, N.Y. The reference appeared as an abstract in the Federation of American Societies for Experimental Biology, 65th Annual Meeting, Atlanta (1981).

The vaccine employed against Marek's Disease Herpesvirus in chickens was derived from Turkey herpesvirus (HVT). There is no indication that a vaccine against atherosclerosis caused by human herpes virus could be prepared. There is certainly no suggestion to employ a herpes vaccine containing homologous peptide sequences to those of the viral DNA found in strains of the herpes virus that effect humans.

U.S. Pat. No. 4,038,381 discloses a vaccine for the prevention and treatment of vascular conditions, comprising a combination of a tuberculosis antigen with an antiherpetic vaccine. There is no suggestion to employ the four polypeptides of the present invention as the active ingredients in the vaccine. The reference also states that the individual tuberculosis antigen and antiherpetic vaccine had no known per se ability in the prevention or treatment of vascular disease.

OBJECT OF THE INVENTION

It is the object of the invention to provide a vaccine as a prophylaxis against pathogenic development of atherosclerotic plaque in a mammalian subject susceptible thereto.

SUMMARY OF THE INVENTION

We have found such a vaccine that is effective as a prophylaxis against pathogenic development of atherosclerotic plaque in mammalian subjects, including humans. The vaccine contains four new polypeptide sequences as described herein below in the indicated proportions:

(a) 10 to 30% by weight of the compound

Ala Pro Leu Pro Ala Pro Ala Pro Pro Ser Thr Pro Pro Gly      (Seq ID 2)
 1           5                    10

Pro Glu Pro Ala Pro Ala Gln Pro Ala Ala Pro Arg Ala Ala ;
    15              20            25

(b) 10 to 30% by weight of the compound

Ala Pro Pro Glu Ala Asp Ala Arg Thr Leu Arg Arg       (Seq ID 4)
 1           5                    10

Pro Gly Pro Pro Leu Pro Leu Pro Pro Ser Leu Leu Pro;
    15                  20              25

(c) 10 to 30% by weight of the compound

Gly Thr Asp Gly Pro Ala Arg Gly Gly Gly Ser Gly       (Seq ID 6)
 1           5                    10

Gly Gly Arg Gly Pro Gly Gly Gly Arg Gly Gly Pro Arg Gly;
    15              20              25 and (d) 10 to 30% by weight of the compound

Gly Trp Ala Ala Arg Arg Gly Arg Arg Arg Gly Arg       (Seq ID 8)
 1           5                    10

Arg Arg Gly Arg Arg Arg Arg Gln Arg Arg Ala Ala Arg Arg
    15                  20              25

Arg Arg;

in combination with a pharmaceutically acceptable inert vaccine carrier such as normal saline or a physiological oil (e.g. corn oil, sunflower oil).

Preferably each of the four polypeptides is present in the compositions in equal proportions by weight: that is the compositions preferably contain 25% of each of the four polypeptides.

The compositions are prepared by incorporating each of the four polypeptides in the pharmaceutically acceptable inert vaccine carrier such as normal saline or a physiological oil in an adequate concentration of said polypeptides. Preferably there is present 1.0 to 100 µg of each polypeptide per ml of pharmaceutical composition. More preferably one dose of vaccine (1 ml) contains equal parts (20 µg) of each of the 4 polypeptides. Thus the preferred total amount of polypeptides in one dose of vaccine is 80 µg.

Since each of the polypeptides is itself a new compound, each of them, individually, as well as collectively, is considered to be part of the invention as well.

Also contemplated to be within the scope of the invention is a method of prophylaxis of pathogenic development of atherosclerotic plaque in a mammalian subject susceptible thereto which comprises the step of administering to said mammalian subject, a therapeutically effective amount of the pharmaceutical composition containing the four polypeptide sequences as described hereinabove.

The compositions may preferably be administered to a mammalian subject parenterally, such as by injection. More preferably the compositions are administered by subcutaneous, intramuscular, intra-arterial, intravenous or intradermal injection. A preferred dosage of the compositions is 1 ml every 20 days administered in a series of 6 intramuscular injections. The full cycle of treatment may consist of 2 or 3 such courses with 3 month intervals in between.

Use of an adjuvant, for instance inorganic gels such as alum, aluminum hydroxide or aluminum phosphate that increase antigenic response, is optional in the compositions.

Preparation of the Vaccine against Atherosclerosis

The vaccine may be prepared by recombinant DNA techniques or by conventional polypeptide synthesis. When preparing the vaccine by recombinant DNA techniques the following steps are employed:

1. Accumulation of Virus Particles

For isolation of the polypeptides having Seq ID 2 and Seq ID 6, it is necessary to accumulate Herpes Simplex Virus Type 1, and for isolation of the polypeptides having Seq ID 4 and Seq ID 8, it is necessary to accumulate Human Cytomegalovirus.

Herpes Simplex Virus 1 and Human Cytomegalovirus are each cultivated in diploid human embryonic lung cells (HECL).

Tissue Cultures

For isolation of Herpes Simplex Virus 1 and Human Cytomegalovirus, it is necessary to use diploid human embryonic lung cells (e.g. semi-continuous cells). These cells are derived from embryonic lung tissue and following initial dispersal, they can be redispersed and regrown many times (30 to 50 times). Human embryonic lung tissue, which can be obtained from embryos of 10 to 12 weeks, provide a most valuable source for harvesting a number of different herpes viruses, including Herpes Simplex Viruses and Human Cytomegalovirus.

Semi-continuous cells have a normal chromosome count (diploid) and show the phenomenon of contact inhibition. An inoculum of each virus listed above is placed on the monolayer and allowed to absorb for 1 hour. It is then removed and fresh medium is added. Cultures are incubated at 37° C. and they are inspected regularly by microscopy for evidence of virus growth. The culture medium is normally changed on the day after inoculation to minimize the effect of toxins that may persist in the inoculum, and is then replaced periodically to replenish the supply of nutrients for the cells. Cultures are incubated for various lengths of time depending on the virus. While the cytopathic effects of a concentrated inoculum of herpes virus may appear overnight, a low level of cytomegalovirus may take 3 to 4 weeks to appear.

The cells infected by herpes viruses may be cultivated in suspension also.

For inoculation of the tissue cultures to prepare the peptide vaccines, the following viruses may be used:

Herpes Simplex Type 1 (Human herpesvirus 1, Herpesvirus homines type 1) ATCC VR-539, Strain MacIntyre.

Cytomegalovirus ATCC VR-538 Strain: AD-169.

2. Isolation of the following four Polynucleotide Sequences from the Viral DNA that Code for the Four Polypeptides indicated above:

| GCC | CCC | CTC | CCC | GCG | CCC | GCG | CCC | CCC | TCC | ACG | CCC | CCG | GGG | CCC | GAG | 48 |
|---|---|---|---|---|---|---|---|---|---|---|---|---|---|---|---|---|
| Ala | Pro | Leu | Pro | Ala | Pro | Ala | Pro | Pro | Ser | Thr | Pro | Pro | Gly | Pro | Glu | |
| 1 | | | | 5 | | | | | 10 | | | | | 15 | | |

| CCC | GCC | CCC | GCC | CAG | CCC | GCG | GCG | CCC | CGG | GCC | GCC | 84 (Seq ID 1); |
| Pro | Ala | Pro | Ala | Gln | Pro | Ala | Ala | Pro | Arg | Ala | Ala | |
|     |     |     | 20  |     |     |     |     | 25  |     |     |     | |

| GCT | CCT | CCA | GAG | GCC | GAC | GCG | CGG | ACC | CTC | CGA | CGT | CCT | GGC | CCG | CCG | 48 |
| Ala | Pro | Pro | Glu | Ala | Asp | Ala | Arg | Thr | Leu | Arg | Arg | Pro | Gly | Pro | Pro | |
| 1   |     |     |     | 5   |     |     |     |     | 10  |     |     |     |     | 15  |     | |

| CTG | CCG | CTG | CCG | CCT | TCC | CTT | CTC | CCG | 75 (Seq ID 3); |
| Leu | Pro | Leu | Pro | Pro | Ser | Leu | Leu | Pro | |
|     |     |     | 20  |     |     |     |     | 25  | |

| GGC | ACC | GAC | GGC | CCC | GCC | CGA | GGA | GGC | GGA | AGC | GGA | GGA | GGA | CGC | GGC 48 |
| Gly | Thr | Asp | Gly | Pro | Ala | Arg | Gly | Gly | Gly | Ser | Gly | Gly | Gly | Arg | Gly |
| 1   |     |     |     | 5   |     |     |     |     | 10  |     |     |     |     | 15  | |

| CCC | GGT | GGC | GGA | AGA | GGT | GGC | CCC | CGC | GGG | 78 (Seq ID 5); and |
| Pro | Gly | Gly | Gly | Arg | Gly | Gly | Pro | Arg | Gly | |
|     |     |     | 20  |     |     |     |     | 25  |     | |

| GGC | TGG | GCT | GCG | CGG | CGG | GGC | CGG | CGA | CGG | GGA | CGG | CGG | CGG | GGA | CGA 48 |
| Gly | Trp | Ala | Ala | Arg | Arg | Gly | Arg | Arg | Arg | Gly | Arg | Arg | Arg | Gly | Arg |
| 1   |     |     |     | 5   |     |     |     |     | 10  |     |     |     |     | 15  | |

| CGT | CGC | CGC | CAG | CGG | CGA | GCG | GCA | CGG | AGA | CGG | AGG | 84 (Seq ID 7) |
| Arg | Arg | Arg | Gln | Arg | Arg | Ala | Ala | Arg | Arg | Arg | Arg. | |
|     |     |     | 20  |     |     |     |     | 25  |     |     |     | |

Note the DNA sequences assigned Seq ID numbers 1,3,5, and 7 are the gene sequences containing the codons to obtain the polypeptides having Seq ID Nos. 2,4,6, and 8. The DNA fragments having Seq ID Nos 1,3,5, and 7 are regarded as novel intermediate compounds that constitute part of the present invention.

The Origin and Utility of these Four Polynucleotides

The polynucleotide of Seq ID 1 is the part of the Herpes Simplex Virus Type 1 immediate early (IE) gene 3 for the transcriptional activator IE 175 (=ICP 4). Its 84 nucleotides are located from bp 3760 up to 3844 according to the known gene nucleotide sequence Herpes Simplex Virus Type 1, Viridae; DS-DNA Enveloped Viruses; Herpes Viridae; Alpha-Herpes Virinae. This same polynucleotide may also be found in the complete short unique region 2 with partial terminal and inverted repeats in DNA, HSV 1, Strain 17.

The polynucleotide of Seq ID 3 is the part of the Human Cytomegalovirus (Strain AD 169) complete genome (from base pair 70001 up to base 80100). Its 75 nucleotides are located from bp 2342 up to 2416 in this region of the Human Cytomegalovirus gene Strain AD=169 according to Human Cytomegalovirus, Viridae, DS-DNA Enveloped Viruses, Herpesviridae, Betaherpesvirinae.

The polynucleotide of Seq ID 3 is in the Human Cytomegalovirus F fragment DNA encoding DNA Polymeraseycoprotein B also and has homology with DNA from the following viruses:

(a) Epstein-Barr Virus, artifactual joining of B95-8 complete gene and the sequences from ragi of the large deletion found in B95-8 (from base pair 70001 to 80100) about 70%.

(b) HSV1 (strain 17) complete short unique region with inverted repeat DNA, (from bp 10001 to 20100) about 65%.

(c) HSV20RF1, ORF2, and ORF 3 (LAT) gene about 65%.

The polynucleotide with Seq ID5 is the part of Herpes Simplex virus type one (HSV 1) latency associated transcript (LAT).

Its 78 nucleotides are localized from 2255 up to 2332 positions of LAT gene according to Herpes Simplex Virus Type 1, Viridae, DS-DNA Enveloped Viruses; Herpes Viridae, Alpha-Herpes-virinae.

This polynucleotide has homology:
with Herpes Simplex virus type 1 Bam Hl fragment B DNA sequence—about 97.5 %:
with Herpes Simplex virus type 1 gene encoding two latency—related proteins—about 97.5%;
with Pseudorabies virus immediate—early gene—about 70%;
with Herpes Simplex virus type 20RF1, ORF2, and ORF3 (LAT) gene —about 70%;
with Epstein-Barr virus, artifactual joining of B95-8 complete genome and the sequences from raji of the large deletion found in B95-8 (from base 70001 to 80100— about 65.5%;
with Bovine Herpesvirus type 1 early—intermediate transcription
control protein (BICP4) gene—about 70%.;
with Human Cytomegalovirus UL56 gene—67.5%;

The polynucleotide with Seq ID 7 is part of Human Cytomegalovirus (HCMV) short unique region, short repeats, and part of long repeat (from base 1 to base 10100).

Its 84 nucleotides are localized from 5340 up to 5424 positions in this part of genome according to Human Cytomegalovirus, Viridae; DS-DNA Enveloped Virules; Herpes Viridae; Betaherpesvirinae This polynucleotide has homology:
with Equine Herpesvirus 4 (EHV4) genome, thymidine kinase (TK) and glycoprotein H (GH) genes—about 71%
with Herpes Simplex virus type 2 immediate—early (IE5) protein mRNA, 5' end—about 65%;
with Herpes Simplex virus type 1 complete genome from base 70001 to base 80100—about 65.5%.

Isolation of the polynucleotides sequences from the vital DNA that code for the four peptides indicated above.

The viral DNA is isolated from corresponding viral suspension obtained from HELC infected by Herpes Simplex 1 or Human Cytomegalovirus (see above about cell cultures and virus strains), purified by agarose gel electrophoresis (AGE) according to Myers, R. M et al, "Detection and Localization of Single Base Changes by Denaturing Gradient Gel Electrophoresis; Methods Enzymol. 155:501 to 527 (1987) and Myers et al, "In Genome Analysis: A Practical Approach" (Ed. K. Davies) p. 95 IRL Press, Oxford (1988), treated by restriction enzymes and subjected by polyacrylamide gel electrophoresis.

The isolation of polynucleotide with Seq ID 1 from Herpes Simplex virus type I immediate early (IE) gene 3 for transcriptional activator IE 175 (=ICP4) is produced after treating DNA by restriction enzyme NcoI with recognition sequence CGATGG. This procedure according to PAAG, EF gives the polynucleotide with 2308 pair of bases (from 2637 up to 4935 position) with the actual fragment located from 3760 up to 3844 position.

The isolation of polynucleotide with Seq ID 3 from HCMV (strain AD169) complete genome is produced after treating of DNA by restriction enzyme Bst E III with recognition sequence GATC. This procedure after PAAG, EF gives the polynucleotide with 2182 pair of base—from 715 to 2898 position—with the actual fragment from 2342 up to 2416 position.

The isolation of polynucleotide with Seq. ID5 from HSVI (LAT) is produced after treating of DNA by restriction enzyme Nco 1 with recognition sequence CCATGG. This procedure after PAAG, EF gives the polynucletide with 1737 pair of base—from 659 up to 2396 position—with actual fragment from 2255 up to 2332 position.

The isolation of polynucleotide with Seq ID 7 from HCMV —short unique region, short repeats, and part of long repeat is produced after treating of DNA by restriction enzyme Nco 1 also. This procedure after PAAG, EF gives the polynucleotide with 4807 pair of base with actual fragment from 5340 up to 5424.

The structures of the Herpes Simplex Virus Type I Immediate Early (IE) Gene 3 for Transcriptional Activator IE 175; HCMV (Strain AD 169); HSVI (LAT); and HCMV—Short Unique Region are known in the art and may be found in EMBL-37.

BRIEF DESCRIPTION OF THE DRAWING

The above and other objects, features, and advantages will become more readily apparent from the following description, reference being made to the accompanying drawing in which:

FIG. 1 is a map of the expression vector plasmid pRSET.

The construction of recombinant plasmid DNA for expression of the four polypeptides, with Seq Nos. 2, 4, 6 and 8.

All 4 polynucleotides are introduced into a polylinker of plasmid pRSET with sites of restriction, including Nco 1 and Bst E III. This plasmid may be used to transform E. Coli (AB 109 strain). For this aim bacteria are treated with $CaCl_2$ which makes their membranes slightly permeable (competent bacteria). The transformed bacteria are then selected by growing them on a medium containing ampicillin. pRSET is a commercial multicopy expressing vector with a high level of protein expression.

Chemical Synthesis

The four sequences having the formulae Seq. Nos. 2,4,6 and 8 may also be prepared by direct polypeptide synthesis that is well known in the art according to the syntheses employed in *The Peptides,* Schroeder and Luebke, Vol. I, Methods of Peptide Synthesis, Academic Press (1965). Preferably each of the four polypeptides having Seq Nos. 2,4,6 and 8 are synthesized starting from the amino terminal acid and forming the peptide bond between the carboxy terminal of the given amino acid and the amino terminal of the next given amino acids. This procedure is carried out until all of the amino acids needed to make each of the four polypeptides are formed into polypeptide chains.

Where it is necessary to employ an amino-protecting group to protect an N-terminal amino substituent to carry out the synthesis of one or more of the four above-mentioned polypeptides, the approaches of pages 3 through 51 of *The Peptides* may be employed. Where it is necessary to employ a carboxy-protecting group to protect either a C-terminal carboxy group or a carboxy group forming part of a side chain (i.e. Glu, Asp) to carry out the synthesis of one or more of the four above-mentioned polypeptides, the methods of page 52 through 75 of the reference are employed.

Glycine and alanine are relatively simple amino acids common to the presently claimed polypeptides. Where it is necessary to block the amino terminal, carbobenzoxy groups are employed. Where it is necessary to block the carboxy terminal, a benzyl ester is formed. See pages 137 and 138 of *The Peptides.* In fact the information regarding blocking the C- and N-terminals of simple amino acids such as glycine and alanine without highly reactive side chains is still highly relevant to the blocking of all amino acids involved in the synthesis of the polypeptides of the present invention.

One amino acid common to all four polypeptides of the Seq Nos 2,4,6 and 8 is arginine. Arginine has a guanido group on its side chain and sometimes this group ]may be responsible for undesired side reactions. Pages 167 through 174 of *The Peptides* discusses peptide synthesis using a number of different blocking groups to protect the guanido side chain. Pages 175 and 176 discuss peptide synthesis involving arginine where the guanido side chain need not be blocked.

Another amino acid that is well represented among the four polypeptides of this invention is proline. Proline is a heterocyclic amino acid with an imino functional group. Where it is necessary to block the imino group, pages 146 through 148 of *The Peptides* provides details.

Serine is an amino acid present in three of the four new polypeptides. Serine contains a side chain that includes a hydroxy group. In some situations the hydroxy group may undergo undesired side reactions. *The Peptides* on pages 207 through 214 describes peptide synthesis using serine with and without protecting groups for the hydroxy group on the side chain.

Threonine is another amino acid present in three of the four new polypeptides that also contains a side chain having a hydroxy substituent. In some situations the hydroxy group may undergo undesired side reactions. *The Peptides* on pages 214 through 216 describes peptide synthesis using threonine with and without protecting groups for the hydroxy group on the side chain.

Tryptophan is an amino acid present in the new polypeptide of Seq. ID No. 8. Tryptophan is an indole and thus contains an indole nitrogen that can undergo undesired side reactions. Pages 148 through 150 of *The Peptides* describes peptide synthesis using tryptophan.

Glycine and alanine are relatively simple amino acids common to the presently claimed polypeptides. Where it is necessary to block the amino terminal, carbobenzoxy groups are employed. Where it is necessary to block the carboxy terminal, a benzyl ester is formed Where it is necessary during polypeptide synthesis to facilitate the reaction of the C-terminal of a given amino acid or peptide, the activated ester technique as described in *The Peptides* on pages 97 to 108 may be employed.

---

What is claimed is:

1. A polypeptide selected from the group consisting of:

```
Ala Pro Leu Pro Ala Pro Ala Pro Pro Ser Thr Pro Pro Gly       (Seq ID 2)
 1           5                   10

Pro Glu Pro Ala Pro Ala Gln Pro Ala Ala Pro Arg Ala Ala
             15              20              25
``` wherein the polypeptide Seq ID 2 contains only these amino acids;

```
Ala Pro Pro Glu Ala Asp Ala Arg Thr Leu Arg Arg              (Seq ID 4)
 1           5              10

Pro Gly Pro Pro Leu Pro Leu Pro Pro Ser Leu Leu Pro
             15              20              25
``` wherein the polypeptide Seq ID 4 contains only these amino acids;

```
Gly Thr Asp Gly Pro Ala Arg Gly Gly Gly Ser Gly              (Seq ID 6)
 1           5              10

Gly Gly Arg Gly Pro Gly Gly Arg Gly Gly Pro Arg Gly
             15              20              25
``` wherein the polypeptide Seq ID 6 contains only these amino acids; and

```
Gly Trp Ala Ala Arg Arg Gly Arg Arg Arg Gly Arg              (Seq ID 8)
 1           5              10

Arg Arg Gly Arg Arg Arg Arg Gln Arg Arg Ala Ala Arg Arg
             15              20              25

Arg Arg
``` wherein the polypeptide Seq ID 8 contains only these amino acids.

2. A polynucleotide selected from the group consisting of:

| GCC | CCC | CTC | CCC | GCG | CCC | GCG | CCC | CCC | TCC | ACG | CCC | CCG | GGG | CCC | GAG |
|-----|-----|-----|-----|-----|-----|-----|-----|-----|-----|-----|-----|-----|-----|-----|-----|
| Ala | Pro | Leu | Pro | Ala | Pro | Ala | Pro | Pro | Ser | Thr | Pro | Pro | Gly | Pro | Glu |
| 1   |     |     |     | 5   |     |     |     |     | 10  |     |     |     |     | 15  |     |
| CCC | GCC | CCC | GCC | CAG | CCC | GCG | GCG | CCC | CGG | GCC | GCC | (Seq ID 1) | | | |
| Pro | Ala | Pro | Ala | Gln | Pro | Ala | Ala | Pro | Arg | Ala | Ala | | | | |
|     |     |     | 20  |     |     |     |     | 25  |     |     |     | | | | | wherein the polynucleotide Seq ID 1 contains only these nucleic acids;

| GCT | CCT | CCA | GAG | GCC | GAC | GCG | CGG | ACC | CTC | CGA | CGT | CCT | GGC | CCG | CCG |
|-----|-----|-----|-----|-----|-----|-----|-----|-----|-----|-----|-----|-----|-----|-----|-----|
| Ala | Pro | Pro | Glu | Ala | Asp | Ala | Arg | Thr | Leu | Arg | Arg | Pro | Gly | Pro | Pro |
| 1   |     |     |     | 5   |     |     |     |     | 10  |     |     |     |     | 15  |     |
| CTG | CCG | CTG | CCG | CCT | TCC | CTT | CTC | CCG | (Seq ID 3) |
| Leu | Pro | Leu | Pro | Pro | Ser | Leu | Leu | Pro |            |
|     |     |     | 20  |     |     |     |     | 25  |            | wherein the polynucleotide Seq ID 3 contains only these nucleic acids;

| GGC | ACC | GAC | GGC | CCC | GCC | CGA | GGA | GGC | GGA | AGC | GGA | GGA | GGA | CGC | GGC |
|-----|-----|-----|-----|-----|-----|-----|-----|-----|-----|-----|-----|-----|-----|-----|-----|
| Gly | Thr | Asp | Gly | Pro | Ala | Arg | Gly | Gly | Gly | Ser | Gly | Gly | Gly | Arg | Gly |
| 1   |     |     |     | 5   |     |     |     |     | 10  |     |     |     |     | 15  |     |
| CCC | GGT | GGC | GGA | AGA | GGT | GGC | CCC | CGC | GGG | (Seq ID 5) Pro |
| Gly | Gly | Gly | Arg | Gly | Gly | Pro | Arg | Gly |     |                |
|     |     |     | 20  |     |     |     |     | 25  |     |                | wherein the polynucleotide Seg ID 5 contains only these nucleic acids; and

| GGC | TGG | GCT | GCG | CGG | CGG | GGC | CGG | CGA | CGG | GGA | CGG | CGG | CGG | GGA | CGA |
|-----|-----|-----|-----|-----|-----|-----|-----|-----|-----|-----|-----|-----|-----|-----|-----|
| Gly | Trp | Ala | Ala | Arg | Arg | Gly | Arg | Arg | Arg | Gly | Arg | Arg | Arg | Gly | Arg |
| 1   |     |     |     | 5   |     |     |     |     | 10  |     |     |     |     | 15  |     |
| CGT | CGC | CGC | CAG | CGG | CGA | GCG | GCA | CGG | AGA | CGG | AGG | (Seq ID 7) |
| Arg | Arg | Arg | Gln | Arg | Arg | Ala | Ala | Arg | Arg | Arg | Arg |            |
|     |     |     | 20  |     |     |     |     | 25  |     |     |     |            | wherein the polynucleotide Seq ID 7 contains only these nucleic acids.

* * * * *